(12) United States Patent
Kuehn et al.

(10) Patent No.: US 11,439,763 B2
(45) Date of Patent: Sep. 13, 2022

(54) INTEGRATION OF AN ULTRASOUND SENSOR IN A PLUNGER STOPPER OF AN INJECTION DEVICE

(71) Applicant: SANOFI, Paris (FR)

(72) Inventors: Bernd Kuehn, Frankfurt am Main (DE); Michael Schabbach, Frankfurt am Main (DE); Dietmar Hammen, Frankfurt am Main (DE)

(73) Assignee: Sanofi, Paris (ER)

( * ) Notice: Subject to any disclaimer, the term of this patent is extended or adjusted under 35 U.S.C. 154(b) by 228 days.

(21) Appl. No.: 16/763,358

(22) PCT Filed: Nov. 12, 2018

(86) PCT No.: PCT/EP2018/080886
§ 371 (c)(1),
(2) Date: May 12, 2020

(87) PCT Pub. No.: WO2019/096720
PCT Pub. Date: May 23, 2019

(65) Prior Publication Data
US 2020/0330694 A1 Oct. 22, 2020

(30) Foreign Application Priority Data

Nov. 14, 2017 (EP) .................................. 17306574

(51) Int. Cl.
*A61M 5/315* (2006.01)
*A61B 8/00* (2006.01)
*A61M 5/31* (2006.01)

(52) U.S. Cl.
CPC ........... *A61M 5/31566* (2013.01); *A61B 8/56* (2013.01); *A61M 2005/3125* (2013.01);
(Continued)

(58) Field of Classification Search
CPC ...... A61M 5/31566; A61M 2205/3327; A61M 2205/3375; A61M 2205/3561; A61B 8/56
See application file for complete search history.

(56) References Cited

U.S. PATENT DOCUMENTS 5,246,423 A 9/1993 Farkas
5,720,733 A 2/1998 Brown
(Continued)

FOREIGN PATENT DOCUMENTS

CN 106063962 11/2016
EP 2190506 6/2010
(Continued)

OTHER PUBLICATIONS

PCT International Preliminary Report on Patentability in Application No. PCT/EP2018/080886, dated May 19, 2020, 7 pages.
(Continued)

*Primary Examiner* — Bradley J Osinski
(74) *Attorney, Agent, or Firm* — Fish & Richardson P.C.

(57) ABSTRACT

Implementations of the present disclosure are directed to an injection device (102) that includes a medicament reservoir (103), a stopper (105) including a rigid core (125) and an ultrasound probe (122) disposed in a housing, the ultrasound probe configured to transmit an emitted ultrasound signal through the rigid core along a longitudinal direction of the rigid core into the medicament reservoir and to receive an ultrasound signal generated by reflections of the emitted ultrasound signal, the reflections including at least a reflection from a distal end of the medicament reservoir, a control component (124*a*) configured to be electronically coupled with the ultrasound probe and to process the ultrasound signal to generate injection device data, and an antenna (124*c*) configured to be electronically coupled with the
(Continued)

control component and to transmit the injection device data to an external computing device (104).

17 Claims, 6 Drawing Sheets

(52) U.S. Cl.
CPC ............... *A61M 2205/3327* (2013.01); *A61M 2205/3375* (2013.01); *A61M 2205/3561* (2013.01)

(56) References Cited

U.S. PATENT DOCUMENTS

| | | |
|---|---|---|
| 5,921,966 A | 7/1999 | Bendek et al. |
| 6,090,081 A | 7/2000 | Sudo et al. |
| 2002/0016572 A1 | 2/2002 | Beebe |
| 2003/0233075 A1 | 12/2003 | Huegli |
| 2007/0135756 A1 | 6/2007 | Kohlbrenner et al. |
| 2007/0219507 A1 | 9/2007 | Dai et al. |
| 2012/0195182 A1 | 8/2012 | Pommereau et al. |
| 2014/0213975 A1 | 7/2014 | Clemente et al. |
| 2014/0303567 A1 | 10/2014 | Qurishi et al. |
| 2014/0330243 A1 | 11/2014 | Kietzmann et al. |
| 2015/0173342 A1 | 6/2015 | Mitrosky et al. |
| 2015/0174342 A1 | 6/2015 | Mitrosky et al. |
| 2015/0217059 A1 | 8/2015 | Ashby et al. |
| 2016/0022539 A1 | 1/2016 | Daines |
| 2017/0014535 A1 | 1/2017 | Nakamura et al. |
| 2017/0312445 A1 | 11/2017 | Mirov et al. |
| 2017/0316177 A1 | 11/2017 | Mirov et al. |
| 2018/0043102 A1 | 2/2018 | Cojocariu et al. |
| 2018/0078711 A1* | 3/2018 | Krasnow ............ A61M 5/31525 |
| 2018/0193567 A1 | 7/2018 | Schleicher et al. |
| 2018/0200450 A1* | 7/2018 | Lilly ................. A61M 5/31513 |
| 2018/0325728 A1* | 11/2018 | Weikart ................. A61L 31/14 |
| 2020/0114088 A1 | 4/2020 | Schabbach et al. |
| 2020/0188598 A1 | 6/2020 | Schabbach et al. |
| 2021/0001053 A1 | 1/2021 | Kuehn |

FOREIGN PATENT DOCUMENTS

| | | |
|---|---|---|
| JP | H08-206114 | 8/1996 |
| JP | H10-314305 | 12/1998 |
| JP | 2004-162761 | 11/2002 |
| JP | 2007-509652 | 4/2007 |
| JP | 2007-160095 | 6/2007 |
| JP | 2016-510241 | 4/2016 |
| WO | WO 2009/024562 | 2/2009 |
| WO | WO 2009/032399 | 3/2009 |
| WO | WO 2013/064590 | 5/2013 |
| WO | WO 2014/009442 | 1/2014 |
| WO | WO 2014/128155 | 8/2014 |
| WO | WO 2014/145906 | 9/2014 |
| WO | WO 2016/036574 | 3/2016 |
| WO | WO 2016/113409 | 7/2016 |
| WO | WO 2017/070391 | 4/2017 |
| WO | WO 2017/155672 | 9/2017 |

OTHER PUBLICATIONS

PCT International Search Report and Written Opinion in Application No. PCT/EP2018/080886, dated Feb. 6, 2019, 11 pages.
Dielectricmfg.com [online], "Teflon® (Polytetrafluoroethylene, PTFE)," Feb. 27, 2019, retrieved on Oct. 18, 2021, retrieved from URL <https://dielectricmfg.com/knowledge-base/teflon/>, 9 pages.
International Preliminary Report on Patentability in Application No. PCT/EP2018/061110, dated Nov. 5, 2019, 8 pages.
International Preliminary Report on Patentability in Application No. PCT/EP2018/061113, dated Nov. 5, 2019, 9 pages.
International Search Report and Written Opinion in Application No. PCT/EP2018/061110, dated Jun. 13, 2018, 11 pages.
International Search Report and Written Opinion in Application No. PCT/EP2018/061113, dated Jun. 25, 2018, 12 pages.
Matweb.com [online], "Overview of materials for Silicone Rubber," 2017, retrieved on Oct. 18, 2021, retrieved from URL <http://www.matweb.com/search/datasheet.aspx?MATGUID=cbe7a469897a47eda563816c86a73520&ckck=1>, 4 pages.

* cited by examiner

INTEGRATION OF AN ULTRASOUND SENSOR IN A PLUNGER STOPPER OF AN INJECTION DEVICE

CROSS REFERENCE TO RELATED APPLICATIONS

The present application is the national stage entry of International Patent Application No. PCT/EP2018/080886, filed on Nov. 12, 2018, and claims priority to Application No. EP 17306574.9, filed on Nov. 14, 2017, the entire disclosures of which are incorporated herein by reference.

Electronic injection devices allow patients to safely administer a medicament, without the need for constant supervision by medical staff, while enabling transmission of treatment data to the medical staff. Electronic injection devices can include a medicament reservoir like a cartridge or syringe, a sensor, an electric component, a drive system, and an energy supply. The sensor can be integrated in the plunger stopper to determine a plunger position inside a cartridge or the syringe. Further, the sensor can include an ultrasound emitting/receiving sensor.

The stopper is typically made of a material (e.g., an elastomeric material such as butyl rubber) that damps the transmission of the ultrasound signal. Strong ultrasound signals that can be transmitted through the elastomeric material require high energy. Consumption of high energy can be a problem for battery capacity. Further, the thickness of a rubber layer in front of the ultrasound emitting/receiving sensor needs to be very thin and limited in its variability. Conventional rubber molding processes may lack the required precision and thin rubber walls may not be sufficiently stable to withstand manufacturing processes.

Some known mechanical ventricular assist devices have been disclosed in PCT International Publication No. WO 2017/155672, published Sep. 14, 2017, and in U.S. Patent Publication Nos. US 2017/0014535 A1, published Jan. 19, 2017, and US 2015/0174342 A1, published Jun. 25, 2015. These documents disclose ultrasound probes that are integrated in different medical devices such that the surface of the probe is in direct contact with the fluid (e.g., medicament or patient blood stream). The contact of the fluid with the surface of the ultrasound probes systems poses chemical and medical challenges. Common complications of the contact of the fluid with the surface of the ultrasound probes include chemical interactions and contamination of the fluid.

Implementations of the present disclosure include mechanisms and systems configured for measuring an amount of medicament within injection devices. In some implementations, an electronic injection device includes a stopper including a rigid core made of at least one of cyclic olefin copolymer (COC) and a cyclo-olefin polymer (COP) and an ultrasound probe configured to transmit an emitted ultrasound signal through the rigid core along a longitudinal direction of the rigid core into a medicament reservoir and to receive an ultrasound signal generated by reflections of the emitted ultrasound signal, the reflections including at least a reflection from a distal end of the medicament reservoir, a control component configured to be electronically coupled with the ultrasound probe and to process the ultrasound signal to generate injection device data, and an antenna configured to be electronically coupled with the control component and to transmit the injection device data to an external computing device.

In some implementations, the ultrasound signal is within the frequency range of about 2 MHz to about 12 MHz. The ultrasound probe is attached to an inner wall of a closed end of the stopper. The ultrasound probe is coupled to the inner wall of a closed end of the stopper by at least one of a mechanical press fit and a coupling agent. The ultrasound probe is molded within an inner wall of the closed end of the stopper. The ultrasound probe is at a predetermined distance from the outer wall of the stopper in order to detect an amount of medicament within a cartridge included in the injection device. The injection device can include an energy source configured to provide energy to the ultrasound probe and the control component. The injection device data includes an electric signal associated with an amount of medicament within a cartridge included in the injection device. A portion of the rigid core between the ultrasound probe and the medicament reservoir has a thickness from about 0.1 mm to about 4 mm. The ultrasound probe transmits the ultrasound signal after dispensing a portion of a medicament.

In accordance with another aspect of the present invention, a medicament injection system includes: an injection device and an external computing device. The injection device includes a stopper including a rigid core made of at least one of cyclic olefin copolymer (COC) and a cyclo-olefin polymer (COP) and an ultrasound probe configured to transmit an emitted ultrasound signal through the rigid core along a longitudinal direction of the rigid core into a medicament reservoir and to receive an ultrasound signal generated by reflections of the emitted ultrasound signal, the reflections including at least a reflection from a distal end of the medicament reservoir, an control component configured to be electronically coupled with the ultrasound probe and to process the ultrasound signal to generate injection device data, and an antenna configured to be electronically coupled with the control component and to transmit the injection device data. The external computing device configured to receive, process, and display the injection device data.

In some implementations, the external computing device includes one of a mobile device, a smart watch, a tablet, and a laptop. The ultrasound signal is within the frequency range of about 2 MHz to about 12 MHz. The ultrasound probe is attached to an inner wall of the closed end of the stopper. The ultrasound probe is coupled to an inner wall of the closed end of the stopper by at least one of a mechanical press fit and a coupling agent. The ultrasound probe is molded within an inner wall of the closed end of the stopper. The ultrasound probe is at a predetermined distance from the outer wall of the stopper in order to detect an amount of medicament within a cartridge included in the injection device. The medicament injection system can further include an energy source configured to provide energy to the ultrasound probe and the control component. The injection device data includes an electric signal associated with an amount of medicament within a cartridge included in the injection device.

In accordance with another aspect of the present invention, a method for detecting an amount of medicament within an injection device includes generating a trigger associated with an operation of the injection device, in response to generating the trigger, transmitting, by an ultrasound probe, an emitted ultrasound signal that is directed towards a medicament reservoir included in the injection device, the medicament reservoir being separated by a rigid portion of a stopper from the ultrasound probe, the rigid portion of the stopper being made of at least one of cyclic olefin copolymer (COC) and a cyclo-olefin polymer (COP), and receiving, by the ultrasound probe, an ultrasound signal generated by reflections of the emitted ultrasound signal, the reflections including at least a reflection from a distal end of the medicament reservoir, processing the ultrasound signal to generate injection device data, and transmitting the injection device data to an external computing device configured to receive, process, and display the injection device data.

It is appreciated that systems in accordance with the present disclosure can include any combination of the aspects and features described herein. That is to say that methods in accordance with the present disclosure are not limited to the combinations of aspects and features specifically described herein, but also include any combination of the aspects and features provided.

The details of one or more embodiments of the present disclosure are set forth in the accompanying drawings and the description below. Other features and advantages of the present disclosure will be apparent from the description and drawings, and from the claims.

Like reference symbols in the various drawings indicate like elements.

Implementations of the present disclosure are generally directed to mechanisms and systems configured for measuring an amount of medicament within injection devices. More particularly, implementations of the present disclosure are directed to a technique for using radio frequency (RF) signals to determine a volume of a medicament reservoir.

Traditional elastomeric materials, such as butyl rubber, used for plunger stoppers affect the transmission of ultrasound signals. As described in further detail herein, implementations of the present disclosure address this challenge. For example, in accordance with implementations described herein, the plunger stopper can include an ultrasound probe embedded in a rigid material. The composition and the configuration of the plunger stopper provide a plurality of advantages. For example, the features of the plunger stopper optimize functionality and robust performance of an ultrasound probe. The configuration of the plunger stopper is associated with minimum energy consumption. The plunger stopper can include a miniaturized ultrasound probe that has a minimal impact on the overall geometry and size of the plunger stopper. Low dependency of ultrasound signal amplitude on plunger stopper thickness and thickness variation can facilitate production processes. Further, the plunger stopper and ultrasound probe can be manufactured as separate elements (e.g., assembled before or after fill/finish operation of primary container). The separate manufacture can avoid issues associated with heat treatment of sensitive electronic components in an ultrasound probe, such as sterilization processes required for components used in aseptic manufacturing processes. The separate manufacture can avoid issues associated with complex plunger stopper manufacturing processes, such as embedding electronic assemblies as part of stopper forming processes.

Figure 1A:
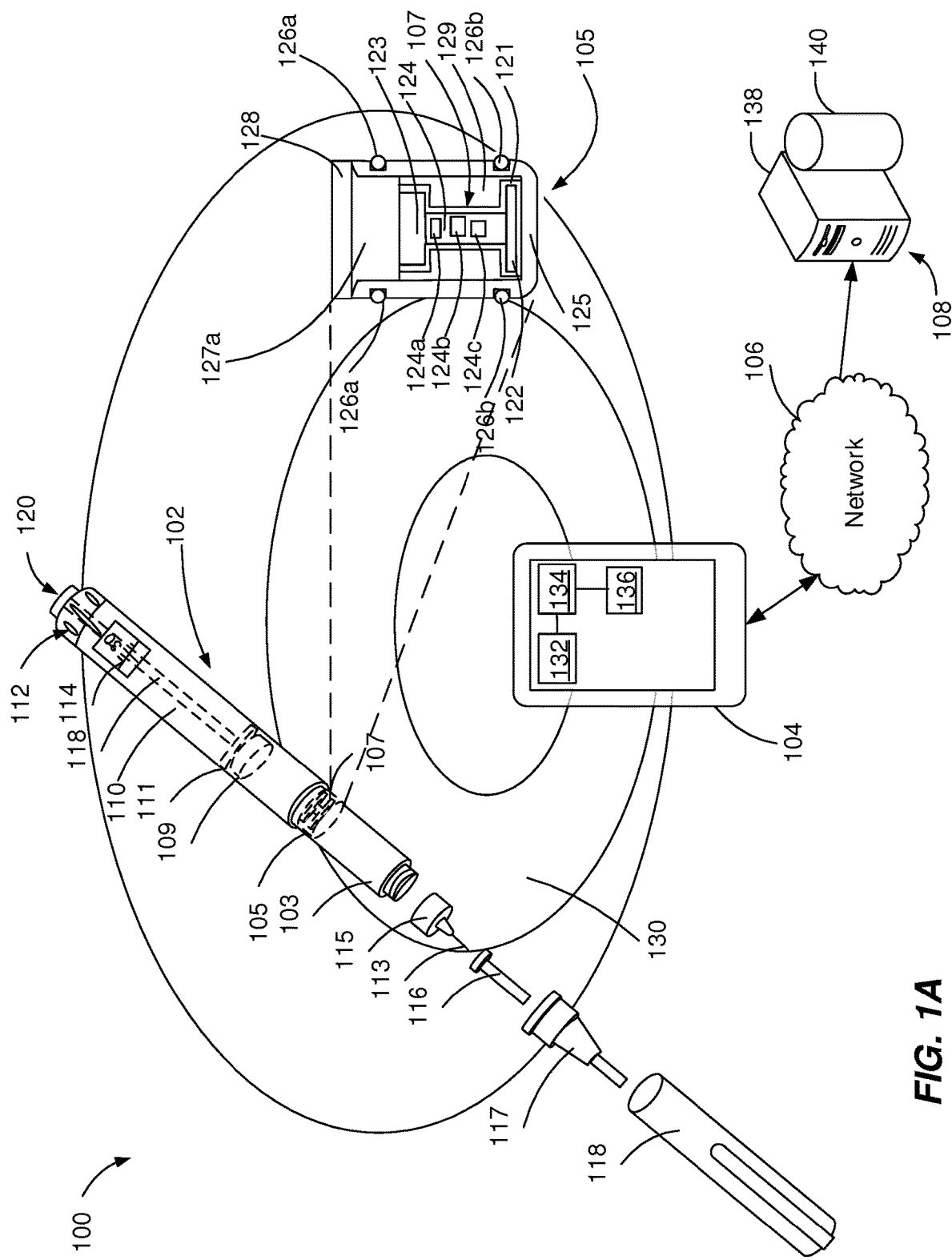
FIGS. 1A-1C are exploded views of examples of devices in accordance with the present disclosure.
Figure 1B:
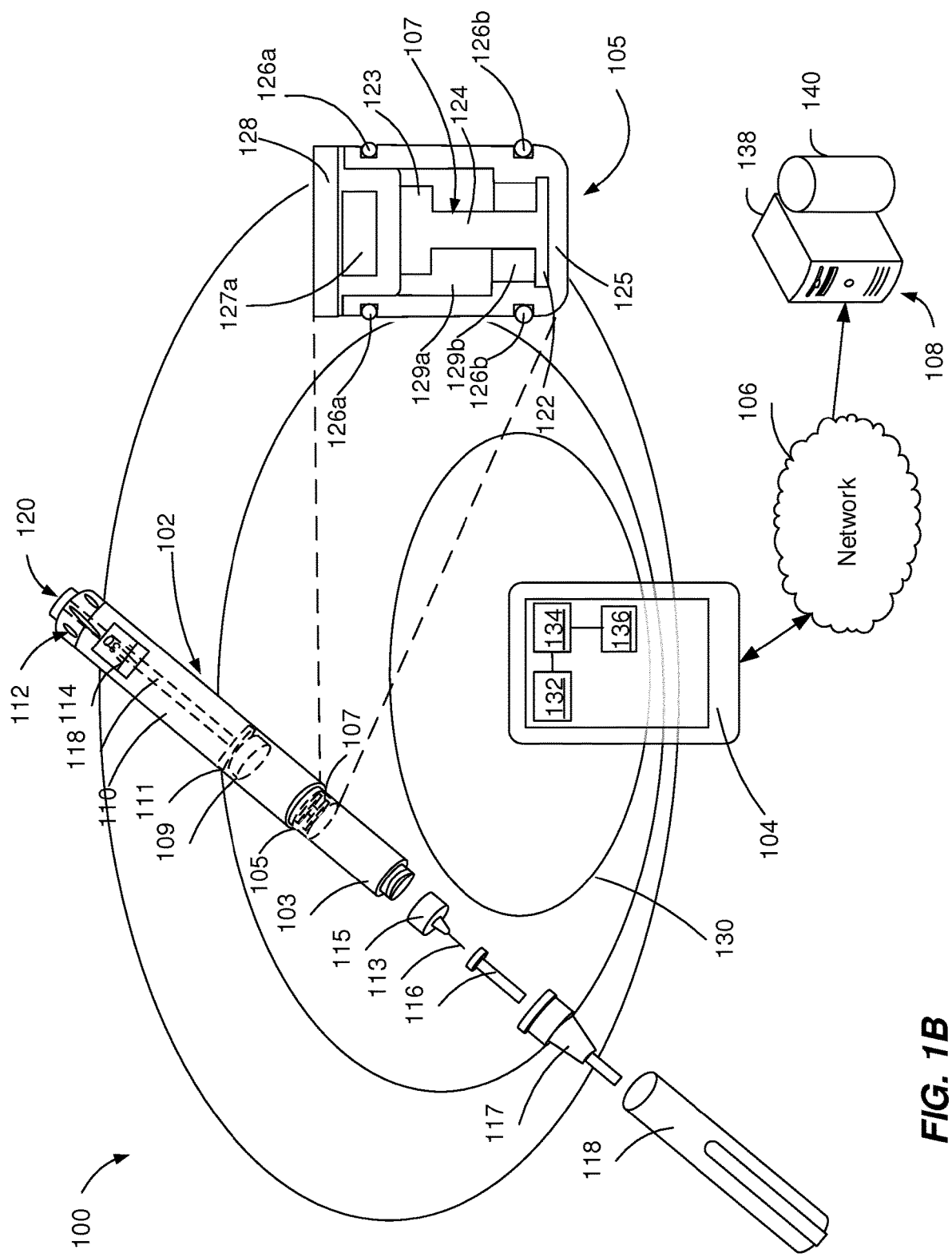
Figure 1C:
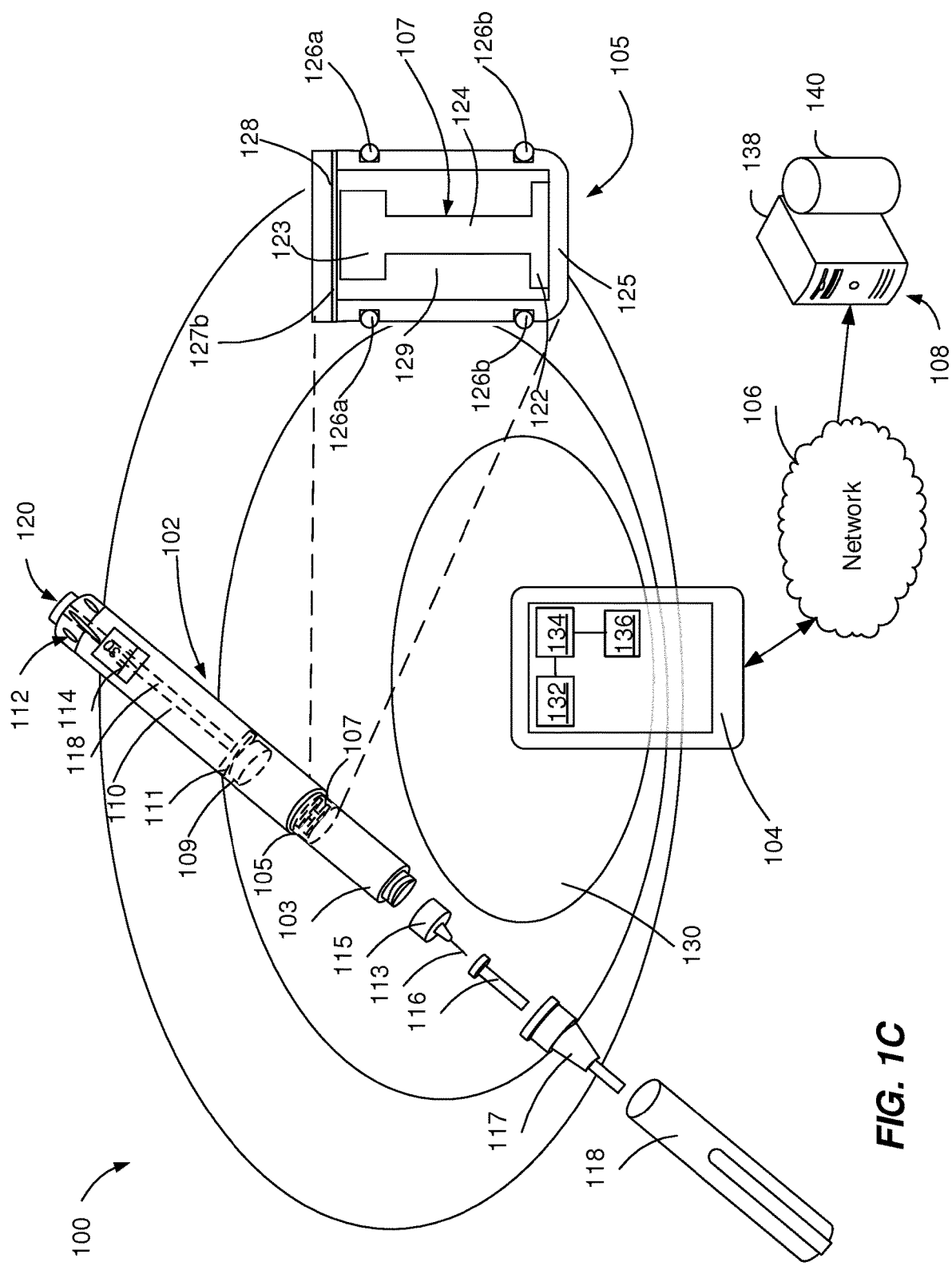

FIGS. 1A-1C illustrate an example system 100 that can be used to execute implementations of the present disclosure. For example, the example system 100 can be used for transmission and reception of ultrasound signals to determine an amount of medicament within an injection device 102. The example system 100 includes one or more injection devices 102, an external device 104, a network 106, and a server system 108.

FIGS. 1A-1C depict an exploded view of an injection device 102 and a close-up view of a cross section of a plunger stopper 105. The injection device 102 can be a pre-filled, disposable injection pen or the injection device 102 can be a reusable injection pen. For example, the injection device 102 can be configured to communicate with the external device 104 and to transmit injection device data to the external device 104; data such as operational data (e.g., date and time of start of usage of injection device 102 and sensor measurements) and corresponding treatment data (e.g., amount of medicament within the injection device 102). In some implementations, the injection device 102 can be associated with an identifier that is used by the external device 104 to uniquely identify the injection device 102.

The injection device 102 can include a housing 110 (e.g., cartridge holder of the injection device 102) and a needle assembly 115. The housing 110 can contain a medicament reservoir 103 (primary container system of the cartridge with closures), the plunger stopper 105, an electronic module 107, a plunger rod 118, a plunger head 109, a bearing 111, a dosage knob 112, a dosage window 114, and an injection button 120. The housing 110 can be molded from a medical grade plastic material. The medicament reservoir 103 can be molded from glass material, such as borosilicate or can be made of medical grade plastic material, such as a polymer including cyclic olefin copolymer (COC) or cyclo-olefin polymer (COP). The medicament reservoir 103 can have a tubular (cylindrical) shape.

The medicament reservoir 103 can be configured to contain a fluid medicament. The medicament can include a pharmaceutical formulation containing at least one pharmaceutically active compound. The medicament can include insulin analogs, insulin derivatives, analgesics, hormones, beta agonists, corticosteroids, or a combination of any of the above-mentioned drugs. The medicament reservoir 103 can be a conventional, generally cylindrical, disposable container like a cartridge or a syringe used to package prepared fluids such as medicaments, anesthetics, and the like. The medicament reservoir 103 can be provided with a pair of ends, one end having a pierceable membrane, which receives an inward end of needle 113 in a liquid tight sealing engagement and the other end being displaceable by the stopper 105. A dose of the contained medicament can be ejected from the injection device 102 by turning the dosage knob 112. The selected dose is displayed by a dosage window 114, for instance in multiples of so-called International Units (IU), wherein one IU is the biological equivalent of about 45.5 micrograms of pure crystalline medicament (1/22 mg). An example of a selected dose displayed in dosage window 114 may for instance be 30 IUs. Turning the dosage knob 112 can cause a mechanical click sound to provide acoustical feedback to a user. The numbers displayed in dosage window 114 can be printed on a sleeve that is contained in housing 110 and mechanically interacts with a plunger head 109 that is fixed at the end of the plunger rod 118 and pushes the plunger stopper 105 of the medicament reservoir 103. In some implementations, the selected dose can be displayed differently, for instance by an electronic display (e.g., the dosage window 114 may take the form of an electronic display). The bearing 111 can provide firm mounting to one or both ends of the plunger rod 118. The plunger head 109 (e.g., a back end of the plunger) can be configured to expel a portion of the fluid by displacing the plunger stopper 105 contained within the medicament reservoir 103, such that a position of the plunger stopper 105 is associated with an amount of the fluid within the injection device 102.

The plunger stopper 105 can include the electronic module 107, a housing 125, a set of elastomeric rings 126a, 126b, a sealing plug 127a, a bearing 128 and a filling 129. One or more features of the plunger stopper 105 can be configured to optimize the operations of the electronic module 107. For example, the housing 125 can be formed of a rigid material that optimizes transmission of the ultrasound signals (e.g., minimizes relative attenuation to approximately under 10%) through the housing 125, as illustrated in Table 1. Accordingly, the housing 125 is sometimes referred to as a rigid core. The rigid material of the housing 125 can include a medical grade plastic material, such as a COC or COP (e.g., ZEONEX®). Table 1 includes results of relative attenuation measurements of the exponential decay of reflections generated by shoulder of the cartridge and the needle pierceable end of the medicament reservoir 103. The results of Table 1 were generated using piezoelectric elements of varying diameters embedded in elastomeric or rigid materials of various thicknesses. The results of Table 1 indicate dependency of ultrasound signal amplitude on plunger stopper thickness for butyl rubber and low (e.g., less than 5%) dependency of ultrasound signal amplitude on plunger stopper thickness for cycloolefin polymer COP (ZEONEX®).

TABLE 1

| Average Peak Signal Amplitude (V) | | Butyl Rubber Thickness (mm) | | | COP Thickness (mm) | |
|---|---|---|---|---|---|---|
| | | 0.8 | 1.0 | 1.6 | 1.0 | 2.0 |
| PZT diameter (mm) | 4.7 | | 0.39 | | 2.89 | 2.95 |
| | 5.6 | | 0.80 | | | |
| | 6 | 2.09 | | 0.97 | 2.82 | 2.95 |
| | 8 | 2.40 | | 0.64 | 2.99 | 2.97 |

In some implementations, a thickness of the housing 125 at the closed end can be selected to maintain a particular distance between the electronic module 107 and the medicament reservoir 103. The distance can be selected based on one or more characteristics of the electronic module 107 (e.g., nearfield of ultrasound probe 122). For example, the thickness of the housing 125 at the closed end can be in the range of approximately 0.1 mm to approximately 1.6 mm. A preferred thickness of the housing 125 is between 0.8 mm and 1.3 mm, a range that provides mechanical stability during processing (e.g. transport, storage, feeding on filling lines, and insertion into cartridge), enables manufacturability of the stopper shell, and prevents attenuation of the ultrasound signal. For example, for rubber molding, the thickness may be about 0.3 mm whereas for injection molding of COC or COP the thickness may be less than 0.1 mm. The thickness of the housing 125 at the closed end can preferably be approximately 1 mm for an ultrasound frequency of 2.8 MHz. In some implementations, a thickness of the lateral walls of the housing 125 can be primarily determined by manufacturability of the housing and mechanical stability during processing (e.g., transport, storage, feeding on filling lines, and insertion into cartridge). In some implementations, the thickness of the lateral walls of the housing 125 can be selected to withstand a force applied during stopper shell insertion into the cartridge and a dispense force applied by the plunger head during dosing of the medicament.

The elastomeric rings 126a, 126b can provide firm mounting of the housing 125 within the medicament reservoir 103 by preventing radial displacement of the housing 125. The bearing 128 can provide firm mounting to the ends of the plunger stopper 105 that is proximal to the plunger head 109. The filling 129 (illustrated in FIGS. 1A and 10) or the filling layers 129a, 129b (illustrated in FIG. 1B) can be configured to keep the electronic module 107 in a firm position within the plunger stopper 105. The sealing plug 127a (illustrated in FIGS. 1A and 1B) or the sealing membrane 127b (illustrated in FIG. 1C) can be optionally fitted on top of the electronic module 107 and can provide a liquid tight sealing engagement to protect the electronic module 107 from humidity or liquid damage. The sealing plug 127a can be fabricated from materials such as medical grade of thermoplastic elastomers, rubber elastomers, and a combination thereof. The plunger stopper 105 can be of a sufficient length so that the plunger stopper 105 is not ripped or twisted when being engaged by the plunger head 109. Further details regarding the plunger stopper 105 are provided with reference to FIGS. 2A-2C.

The needle assembly 115 includes a needle 113 that can be affixed to the housing 110. The needle 113 can be covered by an inner needle cap 116 and an outer needle cap 117, which in turn can be covered by a cap 118. When the needle 113 is inserted subcutaneously or intramuscular in a patient, and the injection button 120 is pushed, the medicament dose displayed in display window 114 can be ejected from injection device 102. When the needle 113 of injection device 102 remains inserted in the patient for several seconds after the injection button 120 is pushed, a high percentage (e.g., approximately 100%) of the dose is injected into the patient's body. Ejection of the medicament dose can generate a mechanical click sound, which can be different from the sounds produced when using dosage knob 112.

The injection device 102 can be used for several injection processes until either medicament reservoir 103 is empty or the expiration date of injection device 102 (e.g., 28 days after the first use) is reached. Before using injection device 102 for the first time, it may be necessary to perform a priming operation to get the plunger head 109 or bearing 111 in contact with the stopper and remove air from medicament reservoir 103 and needle 113. For instance, the priming operation can include selecting two units of medicament and pressing injection button 120 while holding injection device 102 with the needle 113 upwards. The impulse generated by selecting two units of medicament or pressing injection button 120 can initiate an operation of the electronic module 107 and/or communication between the injection device 102 and the external device 104.

The electronic module 107 can be configured to perform and/or assist with one or more functions of the injection device 102 (e.g., the ejection of the medicament). The electronic module 107 can be molded, fitted, or welded within the plunger stopper 105 of the injection device 102. The electronic module 107 can include a housing 121, an ultrasound probe 122, a battery 123, and/or auxiliary components 124. The auxiliary components 124 can include a control component 124a, a sensor 124b, and an antenna 124c.

The housing 121 can be a hermetically closable structure configured to be fitted within a cavity formed in the plunger stopper 105. The housing 121 can enable simultaneous insertion of all components of the electronic module 107 in the plunger stopper 105. The housing 121 can be formed of a rigid material including a medical grade plastic material such as a COC or COP. In some implementations, the thickness of the housing 121 and the thickness of the bottom layer 125 of the plunger stopper 105 can be selected to be substantially equal to or larger than a near field length of the ultrasound probe 122. For example, the thickness of the housing 121 with the thickness of the bottom layer 125 of the plunger stopper 105 can be larger than approximately 1 mm.

The ultrasound probe 122 can be one or more low power single element ultrasound transducers including piezoelectric elements. The ultrasound probe 122 can be powered by the battery 123 to generate an ultrasound signal and to detect a reflection of the ultrasound signal. The diameter of the ultrasound probe 122 can be proportional with the intensity of the generated ultrasound signal, such that increasing the diameter of the ultrasound probe 122 increases the intensity of the generated ultrasound signal (see Table 1). The ultrasound probe 122 can have a diameter of approximately 4 mm to approximately 8 mm. The ultrasound probe 122 can be configured to generate noninvasive ultrasound signals with a frequency of 2 to 12 MHz. In some implementations, multiple ultrasound probes 122, each having a particular frequency can be used, such that the frequency of the ultrasound signal can be changed based on a pre-measured volume of medicament, to increase an accuracy of measurement. The ultrasound signal can be directed towards the medicament reservoir 103. The reflection of the ultrasound signal is associated with the amount of medicament within the medicament reservoir 103. The reflection of the ultrasound signal indicates the reflections generated by each material transition areas intersected by the ultrasound signal, including the boundaries of the medicament reservoir 103. The ultrasound probe 122 can transmit the ultrasound signal to the control component 124a to determine a medicament volume. For example, the stopper position inside the cartridge is determined by evaluation of the time of flight changes when the stopper moves from a first position to a second position. The displacement (difference between the first and second positions) can be correlated to the dispensed medicament volume and thus to the dispensed dose. The sensor 124b can include one or more of a temperature sensor, a humidity sensor, an air quality sensor, a light intensity sensor, or other environmental sensors. The sensor 124b can be powered by the battery 123 to generate sensor data and to transmit the sensor data to the control component 124a.

Coupling of the ultrasound probe to the stopper shell can be done by form fit and mechanical pressure between ultrasound probe and stopper shell. As a further method, coupling agents such as liquid or semi-liquid materials (e.g., silicone oil of different viscosity or silicone gels, wax, hydrocarbons, paraffin and the like) may be used to fill the space between stopper shell and ultrasound probe. In some implementations, adhesives or glues can be used to generate a strong bond between ultrasound probe and stopper shell.

The control component 124a can be an ultra-low power (µW) platform chip and can be configured to control the operations of the electronic module 107. For example, control component 124 can control when the battery 123 powers the ultrasound probe, the sensor 124b, and the antenna 124c. The control component 124 can retrieve energy from the battery 123 to process the ultrasound signal and the sensor data to generate injection device data. The injection device data can include the amount of the fluid in the medicament reservoir 103, additional environmental values measured by the sensor 124b, and an identifier of the injection device 102. The control component 124 can transmit injection device data to the antenna 124c, which can transmit injection device data to the external device 104. The antenna 124c can be a radio frequency (RF) antenna, a bluetooth antenna, a millimeter wave antenna, or any other type of antenna configured for short-range communications within the communication field 130. The communication field 130 can enable communication between the injection device 102 and the external device 104.

The external device 104 can communicate with the injection device 102 over the communication field 130 and with one or more of the server devices 108 over the network 106. In some implementations, the external device 104 can include any appropriate type of computing device such as a desktop computer, a laptop computer, a handheld computer, a tablet computer, a personal digital assistant (PDA), a cellular telephone, a network appliance, a camera, a smart phone, an enhanced general packet radio service (EGPRS) mobile phone, a media player, a navigation device, an email device, a game console, or an appropriate combination of any two or more of these devices, or other data processing devices.

The external device 104 can include a transceiver 132, a processor 134 and a display 136. The transceiver 132 can be configured to transmit signals to activate and/or power the injection device 102 and receive signals from the injection device 102. The transceiver 132 can be configured to spontaneously transmit signals to the injection device 102 at a pre-set frequency during pre-set time intervals. The processor 134 can be configured to process the data transmitted by the injection device 102. The external device 104 can be configured to enable a user to interact with the display 136 (e.g., through a graphical user interface) to initiate a communication between the external device 102 and the injection device 102 (e.g., generate a trigger signal to initiate treatment and select a medicament dose). The display 136 can be configured to display the data received from the injection device 102 and processed by the external processor 132.

In some implementations, the server device 108 includes at least one server 138 and at least one data store 140. In the example of FIG. 1, the server device 108 is intended to represent various forms of servers including, but not limited to a web server, an application server, a proxy server, a network server, and/or a server pool. In general, server systems accept requests for application services and provide such services to any number of client devices (e.g., the external device 104) over the network 106 to support monitoring of usage of the injection device 102. In some implementations, a user (such as a patient or a healthcare provider) can access the application services to analyze past and present data associated with the usage of the injection device 102. The past and present data associated with the usage of the injection device 102 can include dates of medicament injection, expelled doses per date and remaining amount of medicament within the injection device 102.

Figure 2A:
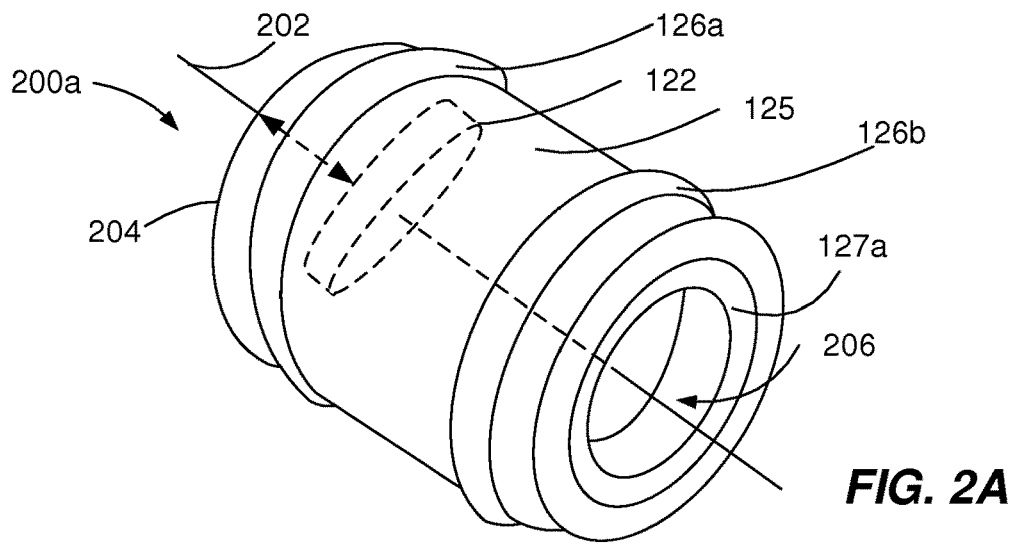
FIG. 2A-2C is a block diagram of an example system architecture that can execute implementations of the present disclosure.
Figure 2B:
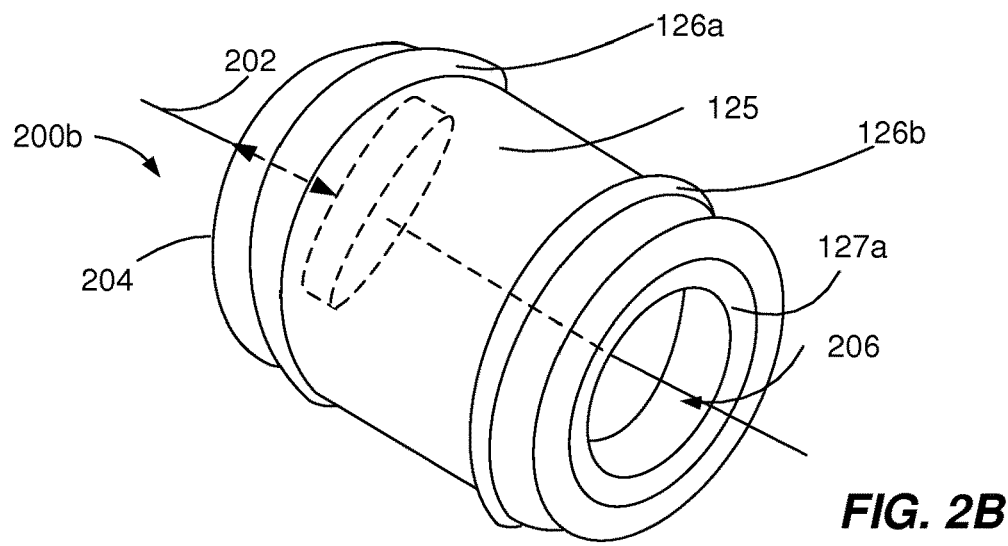
Figure 2C:
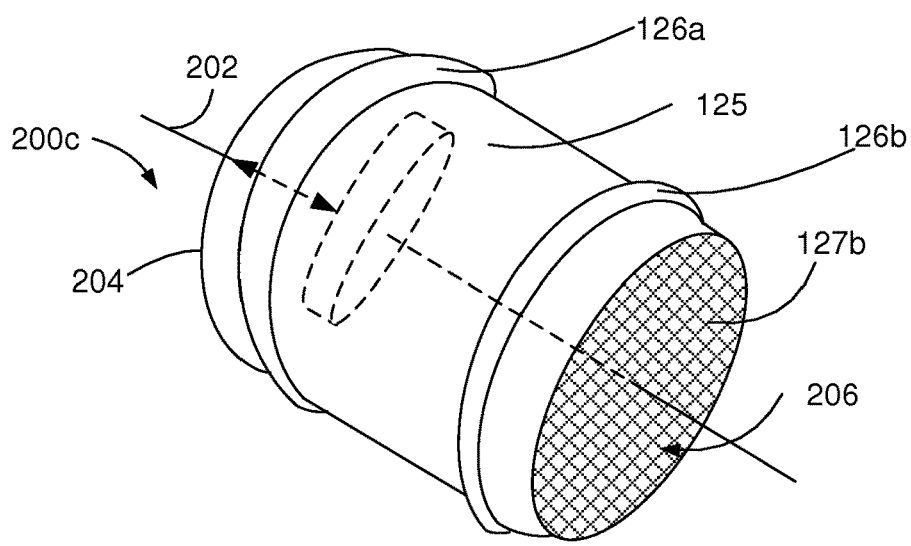

FIGS. 2A-2C illustrate examples of stoppers 200a, 200b, 200c that can be used in implementations of the present disclosure. For example, the stoppers 200a, 200b, 200c may be examples of the plunger stopper 105 described with reference to FIGS. 1A-1C. The example stoppers 200a, 200b, 200c can be configured to optimize transmission of RF signals from and to the ultrasound probe 122, across a closed end 204 of the housing 125 in a longitudinal direction 202 aligned with an axial direction of the medicament reservoir 103. Further, the ultrasound probe 122 can be attached to an inner wall of the closed end 204 of the stoppers 200a, 200b, 200c.

For example, the housing 125 can be formed of a rigid material that optimizes transmission of the ultrasound signals through the housing 125. The housing 125 can have a cylindrical shape or flat cone shape with a closed end 204 and an open end 206. The diameter of the housing 125 is adapted to the inner diameter of the medicament reservoir 103, e.g. a standard cartridge of 3 mL or 1.5 mL nominal fill volume, and to accommodate positioning of sealing rings in the interface between housing 125 and medicament reservoir 103. The outer diameter of the housing 125 is thus typically smaller than the inner diameter of the medicament reservoir 103. In the example shown, the housing 125 is circumferentially surrounded by a set of elastomeric rings 126a, 126b. The elastomeric rings 126a, 126b can have a diameter between approximately 0.8 mm and 2 mm. For example, as illustrated in FIG. 2A, both elastomeric rings 126a, 126b can have an equal diameter of approximately 1 mm, 1.5 mm or 2 mm. As illustrated in FIGS. 2B and 2C, elastomeric ring 126a can have a diameter of approximately 1.5 mm or 2 mm, which can be larger than the diameter of the elastomeric ring 126b (e.g., approximately 1 mm).

The sealing plug 127a (illustrated in FIGS. 2A and 2B) or the sealing membrane 127b (illustrated in FIG. 2C) can be configured to seal the open end 206 of the housing 125 to protect the ultrasound probe 122 from moisture and gas contamination. The sealing plug 127a (illustrated in FIGS. 2A and 2B) can be configured to be fitted or welded within the open end 206 of the housing 125. The fit may be form fit, positive fit, snap-fit, force closure, closed linkage, bonding, or any combination thereof. The sealing plug 127a can seal the open end 206 of the housing 125 with the same material as used for the housing 125 or with a different material (e.g., elastomeric material). The sealing membrane 127b (illustrated in FIG. 2C) can be a sealing film including one or more protection layers. The protection layers of the sealing membrane 127b can include a ceramis layer, a polymer layer and a silicon oxide coating. The sealing membrane 127b can have a thickness of approximately 50 μm to approximately 100 μm, such as approximately 86 μm. The sealing membrane 127b can be attached to the open end 206 of the housing 125 using an adhesive or an attachment feature.

Figure 3:
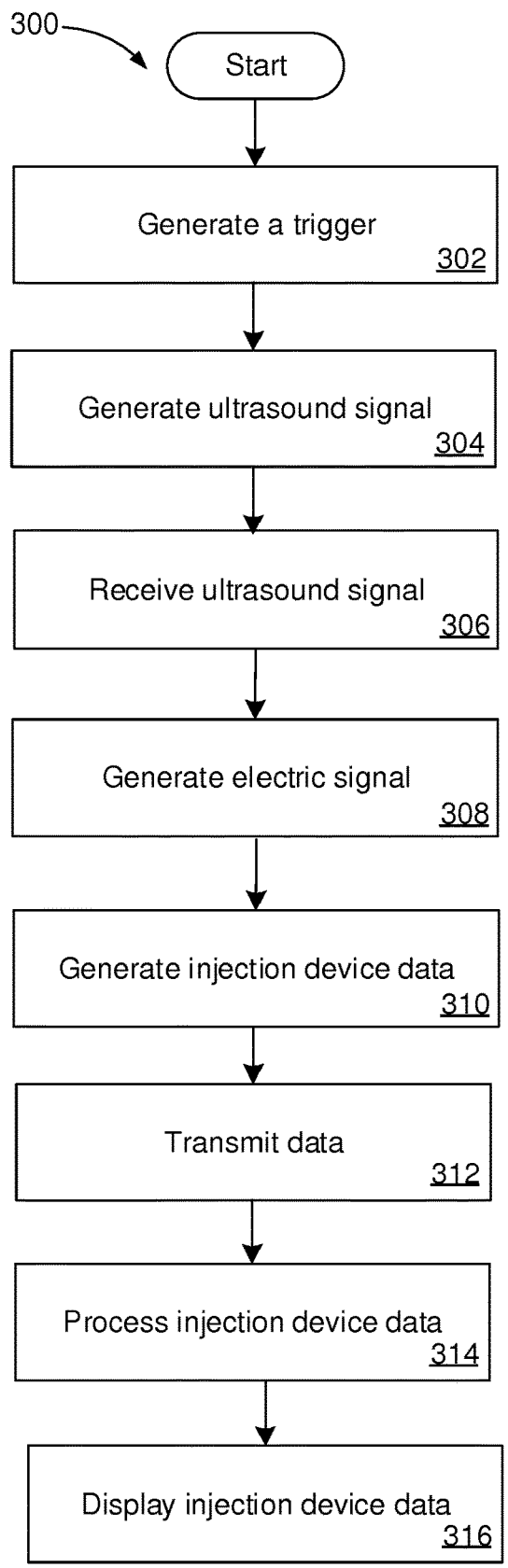
FIG. 3 is a flowchart illustrating an example process that can be executed to perform operations of the present disclosure.

FIG. 3 is a flowchart illustrating an example process 300 that can be carried out, for example, by devices and systems described with reference to FIGS. 1A-C and 2A-C. The process 300 begins by receiving a trigger signal (302). The trigger signal can include a priming operation on an injection device having an ultrasound probe inserted in a rigid plunger stopper. The priming operation can be initiated by a user of the injection device or a user of an external device communicating with the injection device. An example of a priming operation performed with the injection device can include selecting a particular quantity (e.g., one or two) of units of medicament and pressing an injection button while holding the injection device with the needle upwards. Another example of a priming operation performed with the injection device can include pressing a priming button of the injection device configured as an electric switch. In some implementations, the trigger signal can include an interrogation signal generated by an external device. The interrogation signal can be automatically generated by the external device based on one or more conditions. The conditions can include a transmission frequency, a transmission time and/or a time interval. For example, a medicament treatment can be scheduled to be performed within a particular time interval, during which the external device can generate interrogation signals at a given frequency. The signal can be generated by the external device in response to a user input on the external device. For example, a user can interact with an external device to initiate a medicament dispensing service. The trigger signal can include at least one of a mechanical signal, an acoustic signal and an electric signal. The trigger signal can include a command to generate an ultrasound signal.

In response to receiving the trigger signal, an ultrasound signal can be generated by an ultrasound probe located in a rigid plunger stopper of the injection device (304). In some implementations, the frequency of the emitted ultrasound signal can be selected based on a length of a medicament reservoir or a pre-measured or expected volume of medicament. For example, an ultrasound signal with a low frequency (e.g., 2 MHz) can be used for large volumes of medicament and an ultrasound signal with a high frequency (e.g., 10 MHz) can be used for small volumes of medicament. The emitted ultrasound signal is transmitted in a direction parallel with a longitudinal central axis of the stopper and the injection device towards a closed end of the stopper formed of a rigid material. The transmission of the emitted ultrasound signal can include transmission through the rigid material of the stopper and transmission through the medicament stored within the medicament reservoir.

A reflected ultrasound signal is received by the ultrasound probe (306). The reflected ultrasound signal can include reflection from the rigid material of the stopper, reflection from the medicament stored within the medicament reservoir and reflection from a distal end of the medicament reservoir. The terms "distal", "distally" and "distal end" refer to the end of an injection device towards which a needle is provided and which also includes the shoulder area of a cartridge or syringe. The terms "proximal", "proximally" and "proximal end" refer to the opposite end of the injection device, towards which an injection button or dosage knob is provided. One or more features of the reflected ultrasound signal can be indicative of an amount of medicament contained by the medicament reservoir and existence of air bubbles. For example, the reflection from the medicament stored within the medicament reservoir and the reflection from the distal end (e.g., the needle pierceable end) of the medicament reservoir are indicative of an amount of medicament contained by the medicament reservoir.

In response to receiving the reflected ultrasound signal, an electric signal can be generated by the ultrasound probe (308). The electric signal can be used by a processor to generate injection device data (310). The injection device data can include the electric signal, a unique identifier for the injection device, a sensor measurement (e.g., a medicament temperature), an internal clock measurement (e.g., a timestamp of receipt of the ultrasound signal), a location, and/or a situation specific data for the injection device.

The injection device data are transmitted to an external device to analyze one or more parameters associated with the administration of the medicament and the operational conditions of the injection device (312). The injection device data can be transmitted using radio frequency (RF) communication, Bluetooth communication, a millimeter wave communication, or any other appropriate type of short-range communications. The injection device data can be processed by a processor of the external device to generate result data (314). In response to obtaining result data, the result data can be stored for future references and displayed by a graphical user interface of the external device (316). In some implementations, the process 300 is executed before a medicament is expelled by the injection device and repeated after the medicament is expelled by the injection device.

Figure 4:
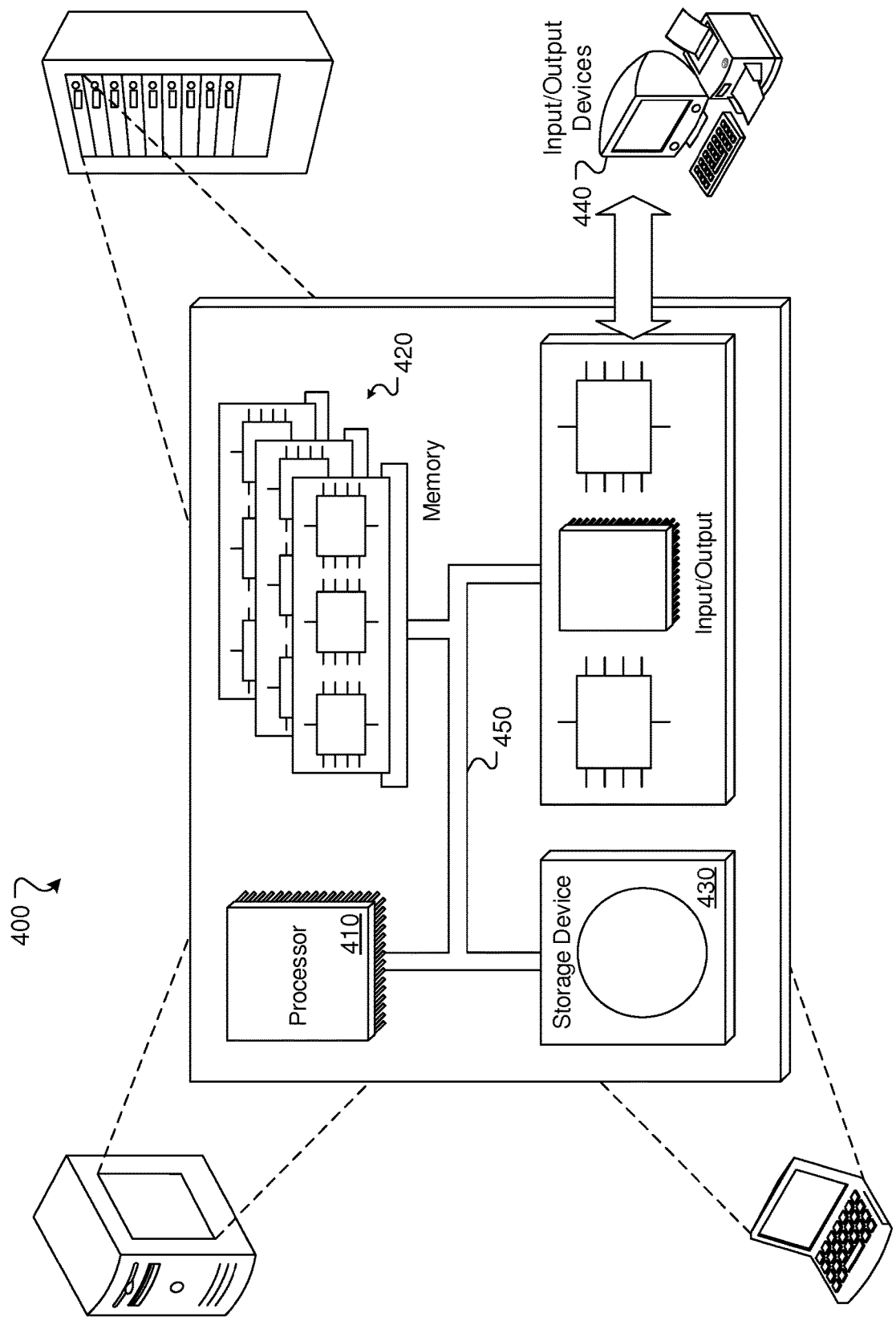
FIG. 4 is a schematic illustration of example computer systems that can be used to execute implementations of the present disclosure.

FIG. 4 shows a schematic diagram of an example computing system 400. The system 400 can be used for the operations described in association with the implementations described herein. For example, the system 400 may be included in any or all of the server components discussed herein (e.g., the server device 108 of FIG. 1). The system 400 includes a processor 410, a memory 420, a storage device 430, and an input/output device 440. Each of the components 410, 420, 430, and 440 are interconnected using a system bus 450. The processor 410 is capable of processing instructions for execution within the system 400. In one implementation, the processor 410 is a single-threaded processor. In another implementation, the processor 410 is a multi-threaded processor. The processor 410 is capable of processing instructions stored in the memory 420 or on the storage device 430 to display graphical information for a user interface on the input/output device 440.

The memory 420 stores information within the system 400. In one implementation, the memory 420 is a computer-readable medium. In one implementation, the memory 420 is a volatile memory unit. In another implementation, the memory 420 is a non-volatile memory unit. The storage device 430 is capable of providing mass storage for the system 400. In one implementation, the storage device 430 is a computer-readable medium. In various different implementations, the storage device 430 may be a floppy disk device, a hard disk device, an optical disk device, or a tape device. The input/output device 440 provides input/output operations for the system 400. In one implementation, the input/output device 440 includes a keyboard and/or pointing device. In another implementation, the input/output device 440 includes a display unit for displaying graphical user interfaces that enable a user to access data related to an item that is collected, stored and queried as described with reference to FIGS. 1-3.

The features described can be implemented in digital electronic circuitry, or in computer hardware, firmware, software, or in combinations of them. The apparatus can be implemented in a computer program product tangibly embodied in an information carrier, e.g., in a machine-readable storage device, for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube) or LCD (liquid crystal display) monitor for displaying information to the user and a keyboard and a pointing device such as a mouse or a trackball by which the user can provide input to the computer.

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include, e.g., a LAN, a WAN, and the computers and networks forming the Internet.

The computer system can include clients and servers. A client and server are generally remote from each other and typically interact through a network, such as the described one. The relationship of client and server arises by virtue of computer programs running on the respective computers and having a client-server relationship to each other.

In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other implementations are within the scope of the following claims.

A number of implementations of the present disclosure have been described. Nevertheless, it will be understood that various modifications may be made without departing from the spirit and scope of the present disclosure. Accordingly, other implementations are within the scope of the following claims.

The invention claimed is:

1. An injection device comprising:
   a medicament reservoir;
   a stopper comprising a rigid housing made of at least one of cyclic olefin copolymer (COC) or a cyclo-olefin polymer (COP) and an ultrasound probe disposed embedded in the rigid housing, the ultrasound probe configured to transmit an emitted ultrasound signal through the rigid housing along a longitudinal direction of the rigid housing into the medicament reservoir and to receive an ultrasound signal generated by reflections of the emitted ultrasound signal, the reflections comprising at least a reflection from a distal end of the medicament reservoir;
   a control component configured to be electronically coupled with the ultrasound probe and to process the ultrasound signal to generate injection device data; and an antenna configured to be electronically coupled with the control component and to transmit the injection device data to an external computing device.

2. The injection device of claim 1, wherein the ultrasound signal is within a frequency range of about 2 MHz to about 12 MHz.

3. The injection device of claim 1, wherein the ultrasound probe is molded within an inner wall of a closed end of the stopper.

4. The injection device of claim 1, the injection device data comprises data associated with an amount of medicament within the medicament reservoir.

5. The injection device of claim 1, wherein a portion of the rigid housing between the ultrasound probe and the medicament reservoir has a thickness from about 0.1 mm to about 4 mm.

6. The injection device of claim 1, wherein the ultrasound probe is a first probe among multiple probes disposed in the stopper.

7. The injection device of claim 1, wherein the stopper includes multiple ultrasound probes, and each ultrasound probe is configured to operate on a respective frequency.

8. A medicament injection system comprising:
    an injection device; and
    an external computing device,
    wherein the injection device comprises:
        a medicament reservoir,
        a stopper comprising a rigid housing made of at least one of cyclic olefin copolymer (COC) or a cyclo-olefin polymer (COP) and an ultrasound probe embedded in the rigid housing, the ultrasound probe configured to transmit an emitted ultrasound signal through the rigid housing along a longitudinal direction of the rigid housing into the medicament reservoir and to receive an ultrasound signal generated by reflections of the emitted ultrasound signal, the reflections comprising at least a reflection from a distal end of the medicament reservoir;
        a control component configured to be electronically coupled with the ultrasound probe and to process the ultrasound signal to generate injection device data, and
        an antenna configured to be electronically coupled with the control component and to transmit the injection device data to the external computing device, and
    wherein the external computing device is configured to:
        receive and process the injection device data; and
        display information related to the processed injection device data.

9. The medicament injection system of claim 8, wherein the external computing device comprises one of a mobile device, a smart watch, a tablet, and a laptop.

10. The medicament injection system of claim 8, wherein the ultrasound probe is embedded in an inner wall of a closed end of the stopper.

11. The medicament injection system of claim 8, comprising an energy source configured to provide energy to the ultrasound probe and the control component.

12. The medicament injection system of claim 8, wherein the injection device data comprises data associated with an amount of medicament within the medicament reservoir.

13. The medicament injection system of claim 8, wherein the stopper includes multiple ultrasound probes, and each ultrasound probe is configured to operate on a respective frequency.

14. A method for detecting an amount of medicament within an injection device, the method comprising:
    generating a trigger associated with an operation of the injection device;
    in response to generating the trigger, transmitting, by an ultrasound probe, an emitted ultrasound signal that is directed towards a medicament reservoir included in the injection device, the medicament reservoir being separated by a rigid portion of a stopper from the ultrasound probe, the rigid portion of the stopper being made of at least one of cyclic olefin copolymer (COC) or a cyclo-olefin polymer (COP), the ultrasound probe being embedded in the rigid portion;
    receiving, by the ultrasound probe, an ultrasound signal generated by reflections of the emitted ultrasound signal, the reflections comprising at least a reflection from a distal end of the medicament reservoir;
    processing the ultrasound signal to generate injection device data comprising the amount of medicament in the medicament reservoir; and
    transmitting the injection device data to an external computing device configured to:
        receive and process the injection device data; and
        display information related to the processed injection device data.

15. The method of claim 14, wherein the ultrasound signal is within a frequency range of about 2 MHz to about 12 MHz.

16. The method of claim 14, wherein the ultrasound probe is molded within an inner wall of a closed end of the stopper.

17. The method of claim 14, wherein an energy source is configured to provide energy to the ultrasound probe.

* * * * *

UNITED STATES PATENT AND TRADEMARK OFFICE
CERTIFICATE OF CORRECTION

| | |
|---|---|
| PATENT NO. | : 11,439,763 B2 |
| APPLICATION NO. | : 16/763358 |
| DATED | : September 13, 2022 |
| INVENTOR(S) | : Bernd Kuehn, Michael Schabbach and Dietmar Hammen |

It is certified that error appears in the above-identified patent and that said Letters Patent is hereby corrected as shown below:

In the Claims

Column 12, Line 56, Claim 1, after "probe", delete "disposed"

Signed and Sealed this
Eighth Day of November, 2022

Katherine Kelly Vidal
*Director of the United States Patent and Trademark Office*